US00PP33304P2

(12) United States Plant Patent
Noack

(10) Patent No.: US PP33,304 P2
(45) Date of Patent: Aug. 3, 2021

(54) ***ROSA* 'NOA16079'**

(50) Latin Name: *Rosa hybrida*
Varietal Denomination: NOA16079

(71) Applicant: Reinhard Noack, Gutersloh (DE)

(72) Inventor: Reinhard Noack, Gutersloh (DE)

( * ) Notice: Subject to any disclaimer, the term of this patent is extended or adjusted under 35 U.S.C. 154(b) by 0 days.

(21) Appl. No.: 17/091,428

(22) Filed: Nov. 6, 2020

(51) Int. Cl.
*A01H 6/74* (2018.01)
*A01H 5/02* (2018.01)

(52) U.S. Cl.
USPC ..... Plt./107

(58) Field of Classification Search
USPC ..... Plt./107
See application file for complete search history.

*Primary Examiner* — Annette H Para
(74) *Attorney, Agent, or Firm* — Cassandra Bright

(57) ABSTRACT

A new and distinct cultivar of *Rosa* plant for garden use named 'NOA16079' is disclosed, characterized by fully double, dark pink flowers with fragrance and very good repeat flowering. Plants have excellent resistance to blackspot, powdery mildew, downy mildew and rust diseases. Plants are well suited for landscape uses and rebloom from Spring until mid-Fall. The new variety is a *Rosa*, normally produced as an outdoor garden or container plant.

2 Drawing Sheets

Figure 1:
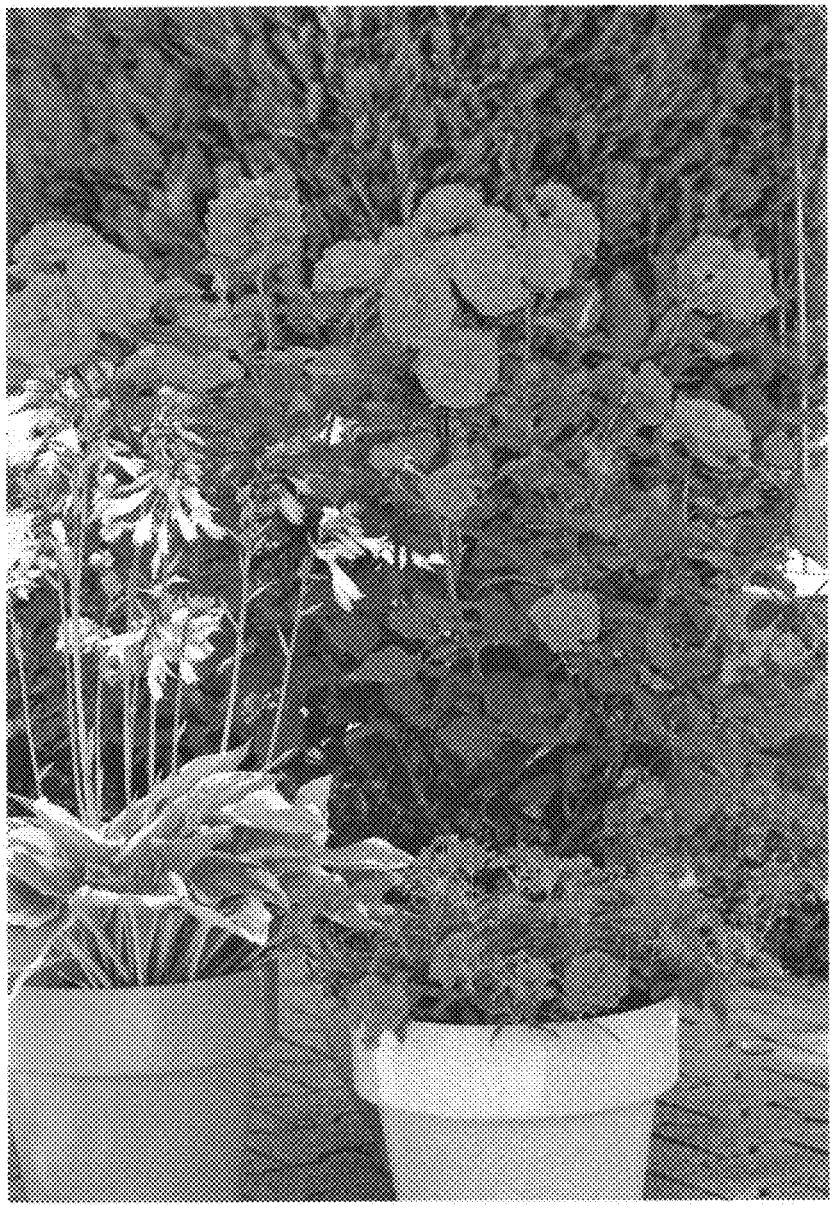

Latin name of the genus and species: *Rosa hybrida.*
Variety denomination: 'NOA16079'.

BACKGROUND OF THE INVENTION

The new *Rosa* cultivar is a product of a planned breeding program conducted by the inventor, Reinhard Noack, conducted in Gutersloh, Germany. The objective of the breeding program was to create a new and distinct shrub rose plants with unique qualities such as, uniform growth and full flowering in combination with fragrance. Additionally, the inventor sought to create new varieties with abundant, attractive, recurrent flowers and attractive, abundant foliage as well as excellent resistance to diseases encountered in landscapes and gardens. These objectives have been substantially achieved and in that distinguish 'NOA16079' from all other varieties of which the inventor is aware. This combination of qualities is not present in prior rose cultivars known to the inventor. The cross resulting in this new variety was made during May of 2007.

The seed parent is an unnamed, unpatented, proprietary *Rosa hybrida*. The pollen parent is a different unpatented, unnamed proprietary *Rosa hybrida*. The new variety was discovered in April of 2008 by the inventor in a group of seedlings resulting from the 2007 crossing, in a research greenhouse in Gutersloh, Germany.

Asexual reproduction of the new cultivar was performed by terminal semi-soft wood vegetative cuttings. This was first performed at a research greenhouse in Gutersloh, Germany in Summer of 2010 and has shown that the unique features of this cultivar are stable and reproduced true to type in successive generations.

SUMMARY OF THE INVENTION

The cultivar 'NOA16079' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NOA16079' These characteristics in combination distinguish 'NOA16079' as a new and distinct *Rosa* cultivar:

1. Dark pink flowers.
2. Very full, double flowers.
3. Plants have excellent resistance to blackspot, powdery mildew, downy mildew and rust diseases.
4. The flowers are strongly fragrant.
5. Suitability for landscape purposes.
6. Long lasting flowers.
7. Long flowering period.
8. Strong peduncles.

Plants of the new cultivar 'NOA16079' are similar to plants of the seed parent, in most horticultural characteristics, however, plants of the new cultivar 'NOA16079' differ in the following:

1. The new variety has dark pink flowers; the seed parent has red flowers.
2. The new variety has a fully double flower; the seed parent has a semi-double flower.
3. The new variety exhibits better disease resistance than the seed parent.

Plants of the new cultivar 'NOA16079' are similar to plants of the pollen parent in most horticultural characteristics, however, plants of the new cultivar 'NOA16079' differ in the following;

1. The new variety has dark pink flowers; the pollen parent has red-pink flowers.
2. Plant habit of the new variety is upright; plant habit of the pollen parent is semi-upright.
3. Flowers of the new variety are fragrant; flowers of the pollen parent have no fragrance.

COMMERCIAL COMPARISON

Plants of the new cultivar 'NOA16079' can be compared to the commercial variety *Rosa* 'Noa1811108', U.S. Plant Pat. No. 28,988. These varieties are similar in most horticultural characteristics, however 'NOA16079' differs in the following:

1. The new variety has a darker pink flower than this comparator.
2. Flowers of 'NOA16079' typically have 13 to 26 petals, flowers of 'Noa1811108' typically have 80 to 90 petals.

Plants of the new cultivar 'NOA16079' can also be compared to the commercial variety *Rosa* 'Noa38121' U.S. Plant Pat. No. 29,039. These varieties are similar in most horticultural characteristics; however, 'NOA16079' differs in the following:

1. The new variety has darker pink flowers with less purple tones than this comparator.
2. Plants of 'NOA16079' are approximately 90 cm in height, plants of 'Noa38121' are typically 60 to 80 cm in height.

BRIEF DESCRIPTION OF THE PHOTOGRAPHS

The accompanying photograph in FIG. 1 illustrates in full color a typical plant of 'NOA16079'. Age of the plant photographed is approximately 1.5 years.

Figure 2:
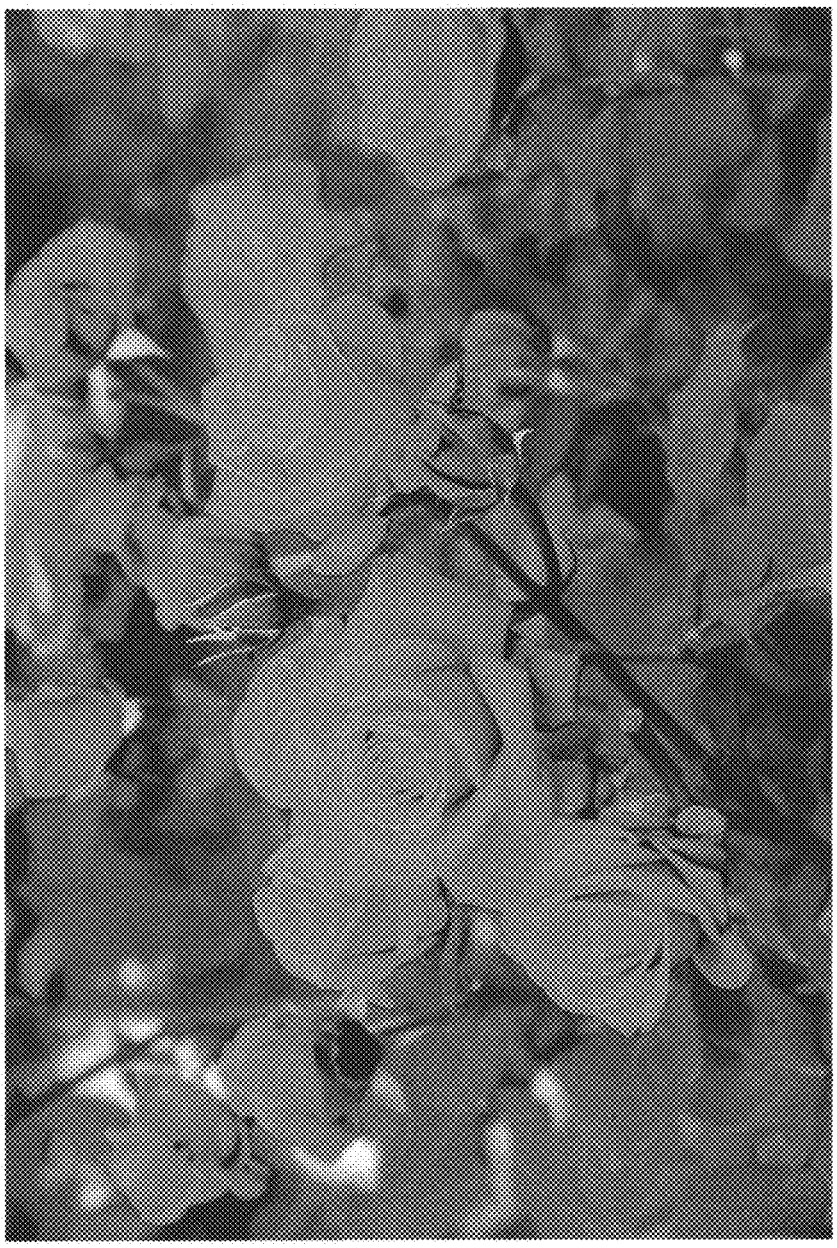

FIG. 2 illustrates a close up view of flowers and buds.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'NOA16079' plants grown outdoors, in Gutersloh, Germany. The growing temperature ranged from approximately −1° C. to 35° C. during the day and from approximately −16° C. to 20° C. during the night. General light conditions are bright, normal sunlight. Measurements and numerical values represent averages of typical plant types.
Botanical classification: *Rosa* 'NOA16079'.
Commercial classification: Shrub rose.

PROPAGATION

Time to initiate roots: About 42 days at approximately 20° C.
Time to produce a rooted cutting: About 90 days at approximately 15° C.

PLANT

Age of plant described: Approximately 3 years, planted in the ground.
Growth habit: Upright.
Mature height: 90 cm.
Mature plant spread: 50 cm.
Rootstock: Own root.
Growth rate: Approximately 80 to 90 cm per year.
Branching characteristics: Sympodial branching.
Length of primary lateral branches: Average 90 cm.
Diameter of lateral branches: Approximately 6 mm.
Quantity of lateral branches: Approximately 5-8.
Branching arrangement: Alternate.
Branches—young wood:
- *Diameter*.—Approximately 3 to 4 mm.
- *Texture*.—Glabrous.
- *Approximately density/quantity of thorns*.—Low density.
- *Color*.—Near Orange-Red 34A.

Branches—old wood:
- *Diameter*.—Approximately 1.5 cm, after 3 years.
- *Color*.—Near Green RHS 143D, with brown tinge not accurately described with R.H.S. chart.
- *Texture*.—Smooth.
- *Approximately density/quantity of thorns*.—Approximately 6 per 10 cm of linear stem.
- *Color of thorns*.—Young: Near Greyed-Orange 171A. Mature: Near Greyed-Orange 173A.
- *Size and shape of thorns*.—Typical deltate thorn, approximately 5 to 10 mm in height and 6 mm at base.

FOLIAGE

Leaf:
- *Arrangement*.—Alternate.
- *Quantity*.—Approximately 25 per main branch.
- *Average length*.—Approximately 12 cm.
- *Average width*.—Approximately 8.5 cm.

Leaflet:
- *Quantity*.—Approximately 5 to 7 per leaf.
- *Average length*.—Approximately 4 cm.
- *Average width*.—Approximately 2.0 cm.
- *Shape of blade*.—Ovate.
- *Apex*.—Acute.
- *Base*.—Obtuse.
- *Margin*.—Serrated.
- *Appearance of top surface*.—Moderately to highly glossy.
- *Appearance of bottom surface*.—Matte.
- *Texture of top surface*.—Non-pubescent.
- *Texture of bottom surface*.—Non-pubescent.
- *Leaf internode length*.—Average 4 to 5 cm.
- *Color*.—Young foliage upper side: Near Green RHS 138A. Strong anthocyanin flushing Greyed-Purple 185A. Young foliage under side: Near Green RHS 138B. Moderate anthocyanin flushing Greyed-Purple 185A. Mature foliage upper side: Near Green RHS 138A. Mature foliage under side: Near Green RHS 138B.
- *Venation*.—Type: Pinnate. Venation color upper side: Near Green 138A. Venation color under side: Near Yellow-Green 150A.

Petiole:
- *Average length*.—Approximately 4 cm.
- *Average diameter*.—Approximately 5 mm.
- *Color*.—Near RHS Greyed-Red 178A.
- *Texture*.—Glabrous, matte.

Rachis:
- *Average length*.—Average range 8.0 to 10.0 cm.
- *Average diameter*.—Approximately 5 mm.
- *Texture*.—Glabrous.
- *Color*.—Near RHS Greyed-Red 178A.

Stipule:
- *Average length*.—Average range 2.0 to 2.5 cm.
- *Average diameter*.—Approximately 1.0 cm.
- *Texture*.—Glabrous.
- *Color*.—Near RHS Green 138A, flushed with anthocyanin Red-Purple 58A.

FLOWER

Natural flowering season: Spring until mid-Fall.
Begins flowering after how many years/months: As early as 3 months from a rooted liner.
Inflorescence type and habit: Fully double flowers occurring 3 to 5 per flowering node. Flowers very full and upwardly cupped.
Rate of flower opening: Approximately 7 days from bud to fully opened flower.
Individual flower size:
*Diameter*.—Approximately 10 cm.
*Depth*.—Approximately 5 cm.
Pedicel:
*Length*.—5 to 6 cm.
*Diameter*.—7 mm.
*Texture*.—Glabrous.
*Color*.—Near RHS Green 138B.
Petals:
*Petal arrangement*.—Formal, rotate, overlapping.
*Size*.—Length: Average 3 to 4 cm. Width: Average 2 to 3 cm.
*Shape*.—Obovate.
*Margin*.—Entire, non-ruffled.
*Apex*.—Obtuse, rounded.
*Base*.—Obtuse.
*Petal quantity*.—Average range 13 to 26.
*Texture*.—Smooth.
Color: Petals:
*When opening*.—Upper surface: Near RHS Red-Purple 66A. Lower surface: Near RHS Red-Purple 66A.
*Fully opened*.—Upper surface: Near RHS Red-Purple 66A. Lower surface: Near RHS Red-Purple 66A.
Bud:
*Shape*.—Ovate.
*Length*.—Approximately 3 cm.
*Diameter*.—Approximately 2 cm.
*Color*.—Near Red 53B.
Sepals:
*Length*.—1.5 cm.
*Width*.—1.0 cm.
*Shape*.—Lanceolate.
*Color*.—Interior Surface: Near RHS Yellow-Green 147C. Exterior Surface: Near RHS Yellow-Green 147B.
*Texture*.—Densely puberulent interior and exterior surfaces.
*Sepal extensions*.—Weak.
*Quantity*.—Average 5 per flower.
Receptacle:
*Length*.—1.0 cm.
*Width*.—1.5 to 2.0 cm.
*Shape*.—Pitcher shaped.
*Color*.—Near RHS Green 143A.
Fragrance: Moderately strong.

REPRODUCTIVE ORGANS

Stamens:
*Number*.—Approximately 30-40.
*Filament length*.—Approximately 5 mm.
*Filament color*.—Pink, not accurately determined with R.H.S. colour chart.
Anthers:
*Length*.—1 mm.
*Shape*.—Narrow ovate.
*Color*.—Near Greyed-Orange 166A.
*Pollen*.—Color: Near Yellow 15A. Quantity: Abundant.
Pistil:
*Number*.—Approximately 10-15.
*Pistil length*.—Approximately 4 mm.
Style:
*Length*.—Approximately 2 mm.
*Color*.—Light green to cream, not accurately determined with R.H.S. chart.
Stigma:
*Shape*.—Linear.
*Color*.—Light green to cream, not accurately determined with R.H.S. chart.

OTHER CHARACTERISTICS

Seeds and fruits: Not observed to date. Fruits typically dry up, without fully forming.
Disease/pest resistance: Excellent resistance to blackspot, powdery mildew, downey mildew and rust. Average resistance to normal pests of garden roses.

What is claimed is:

1. A new and distinct shrub rose plant named 'NOA16079' as herein illustrated and described.

* * * * *